United States Patent [19]

Simpson et al.

[11] 4,416,659
[45] Nov. 22, 1983

[54] SUSTAINED RELEASE CAPSULE FOR RUMINANTS

[75] Inventors: Barbara E. Simpson, Indianapolis, Ind.; Norman A. Gervais, Hardy, Va.

[73] Assignee: Eli Lilly and Company, Indianapolis, Ind.

[21] Appl. No.: 319,183

[22] Filed: Nov. 9, 1981

[51] Int. Cl.³ .............................................. A61M 7/00
[52] U.S. Cl. ........................................ 604/48; 604/57
[58] Field of Search ................. 604/890, 891, 896, 48, 604/57; 424/14–22, 38; 128/1 R

[56] References Cited

U.S. PATENT DOCUMENTS

| 1,406,509 | 2/1922 | Viol | 604/57 |
| 3,845,770 | 11/1974 | Theeuwes et al. | 604/57 |
| 3,993,058 | 11/1976 | Hoff | 604/57 |
| 4,251,506 | 2/1981 | Laby | 424/22 |
| 4,286,593 | 9/1981 | Place et al. | 604/48 |
| 4,326,522 | 4/1982 | Guerrero et al. | 604/57 |

Primary Examiner—C. Fred Rosenbaum
Assistant Examiner—T. J. Wallen
Attorney, Agent, or Firm—Barnes & Thornburg

[57] ABSTRACT

A sustained release capsule for introduction through the esophagus to the rumen of a ruminant has a tubular barrel containing a body of active composition urged by a piston and spring into sealing engagement with a constriction end wall shaped with a peripheral curved border leading to a frustoconical portion defining a delivery opening, the shape and width of such wall controlling the release rate to the rumen. The open front end of the barrel is closed by a hemispherical cap connected at the center of its convex outer face to a wing having opposite arms normally outstanding at near 90° from the capsule body but resiliently bendable over a long arc along the convex face of the cap to retracted positions for introduction of the capsule through the esophagus. In the rumen, the arms return to near 90° positions to hinder regurgitation of the capsule and to better withstand working and contractions of the rumen.

13 Claims, 11 Drawing Figures

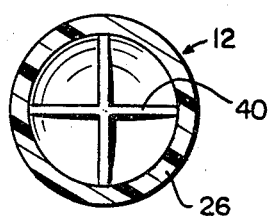
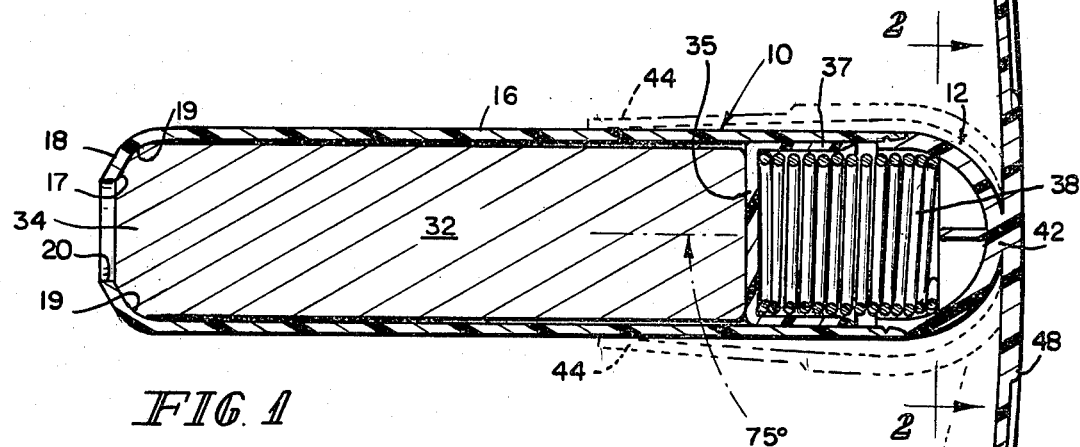
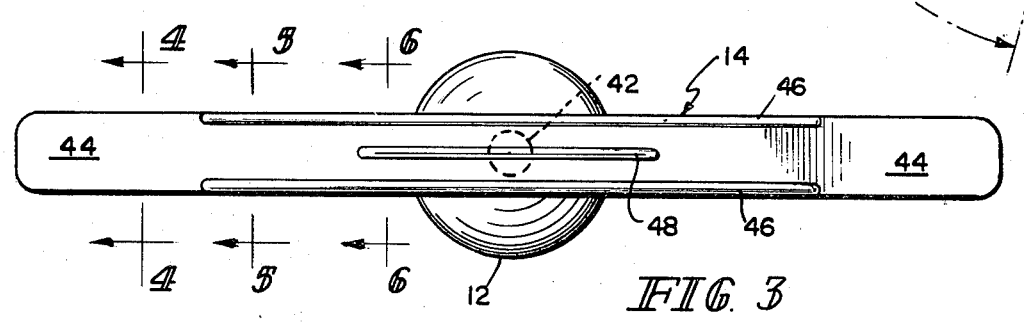
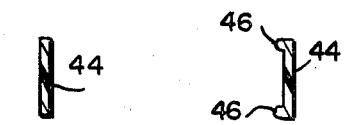
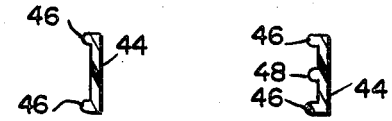
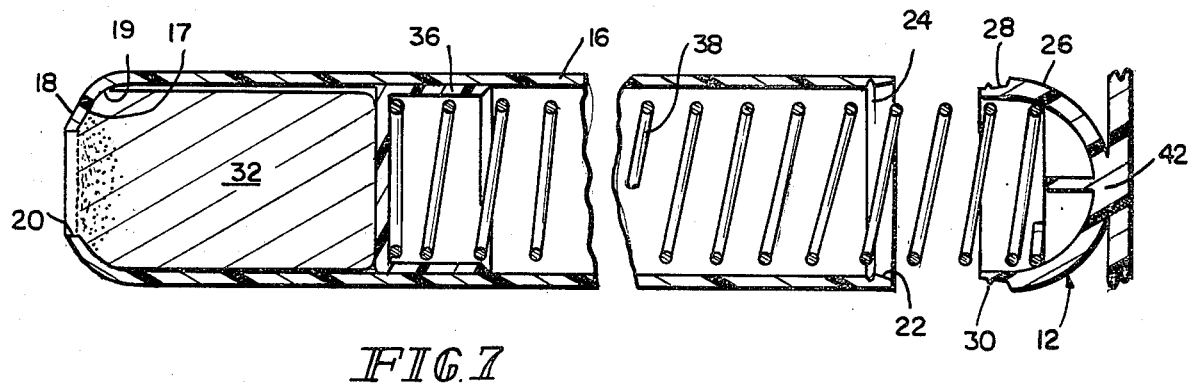

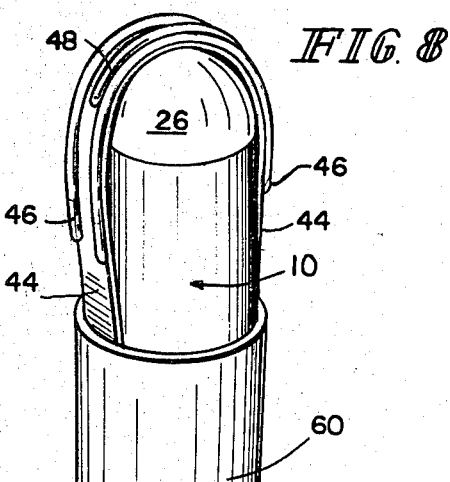
FIG. 8
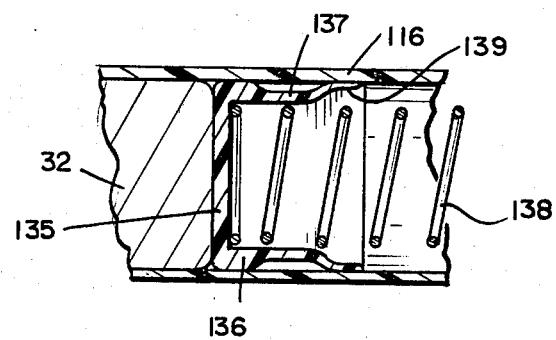
FIG. 9
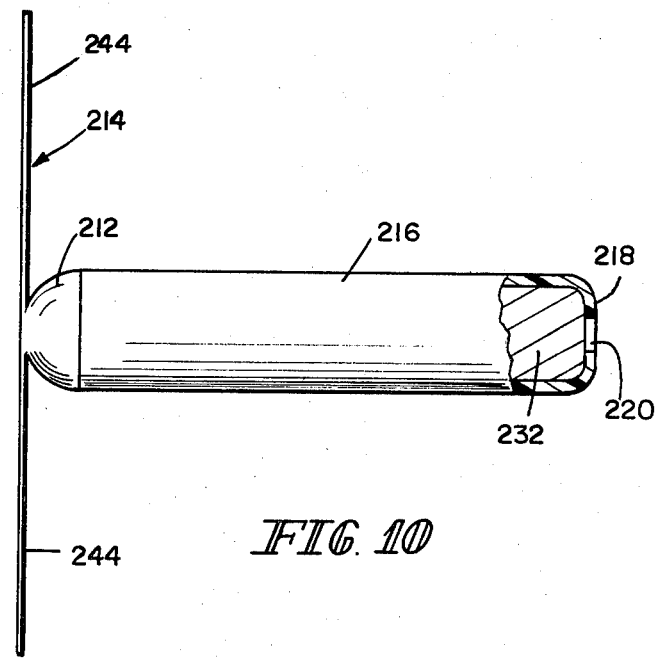
FIG. 10
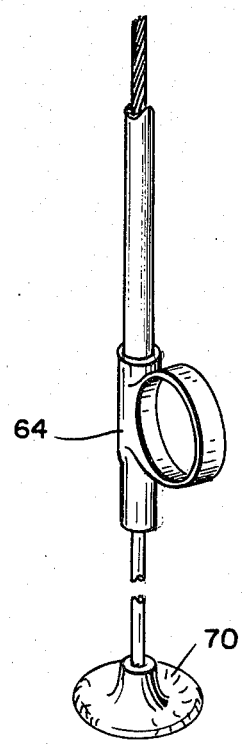
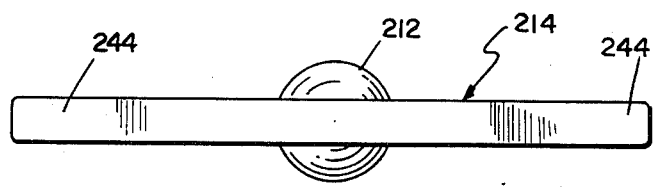
FIG. 11

SUSTAINED RELEASE CAPSULE FOR RUMINANTS

This invention relates to a sustained release capsule for producing continuous administration of a biologically active agent or composition in the rumen of a ruminant animal, especially to provide for the controlled release of such an agent or composition over a prolonged period to range-fed ruminants, such as cattle or sheep.

U.S. Pat. No. 4,251,506, issued Feb. 17, 1981 to Ralph H. Laby, discloses controlled-release compositions for administration of therapeutic agents, including weight-gain promoting agents to ruminants. Other agents which have been proposed for such administration include anti-bloat and anthelmintic agents. Such compositions generally comprise one or more active agents embodied in a solid composition, incuding a waxy carrier and a surfactant. The agents may be dispersed throughout the composition either uniformly or in spaced layers. The patent proposes to enclose a solid plug or charge of the composition in a tubular capsule having a restricted opening at one end and to resiliently urge the plug or charge toward such opening. The capsule is administered per os into the rumen, where the composition containing the active agent will be delivered or eroded into or absorbed by the ruminal fluid at the end opening of the capsule over an extended period. To retain the capsule in the rumen and prevent it from being regurgitated, the capsule of the patent is provided with a pair of resilient arms attached at an acute angle of approximately 45° to the body of the capsule at the delivery end thereof, and it is contemplated that these will be resiliently bent against the tubular body of the capsule when it is inserted through the esophagus of the animal to the rumen, and that such arms will then spring outward to stand at their normal acute angle of approximately 45°, like the barbs of an arrowhead, to retain the capsule in the rumen. Example 10 of the patent reports an experiment in which the growth stimulant monensin sodium was administered to Hereford heifers to produce a substantial weight gain over a trial period of sixty-three days. The patent dislcoses a capsule with its resilient arms at the open or delivery end of the capsule, but it is understood that the patentee has also used capsules on which the angular arms were attached to the closed end of the capsule opposite from the delivery end.

It is the object of the present invention to provide an improved capsule and combination thereof with a medicament-containing charge which will provide more certain and longer lasting retention of the capsule in the rumen, and will also facilitate insertion of the capsule through the esophagus. It is a further object of the invention to provide better control of administration of the composition, with more uniform administration of the medicament over long periods.

In accordance with the invention, the capsule comprises a tubular body having a restricted delivery opening at the rear end and, preferably at the other or front end, an elongated transverse wing having arms extending in opposite directions from the capsule, desirably at substantially right angles to the axis of the capsule. The wing is attached to the capsule adjacent such axis, and the end wall of the capsule is curved rearward from that point of attachment to merge with the side wall of the capsule. The two arms of the wing normally stand outward, but are resiliently bendable rearward along such rear-curved wall to an administration position in which they lie closely along the sides of the tubular body for insertion of the capsule through the esophagus into the rumen. The capsule thus takes a configuration of small effective diameter with a rounded forward end to facilitate insertion through the esophagus, and when the capsule has been deposited in the esophagus, the two arms of the retention wing spring outward to their normal outstanding position where they are effective over a long period to retain the capsule against regurgitation or passage from the rumen.

Preferably, the wings are so constructed and shaped that they are relatively less resistant to bending rearward along the sides of the tubular body than to bending forward away from the tubular body of the capsule. The capsule and the wings are desirably molded of synthetic plastic material, and such preferential bending characteristic may be obtained by forming the arms of the wing with an unsymmetric cross section so as to be bendable more easily in one direction than the other. Also, in some cases, the molded wing may take a slightly arched shape with its concave side toward the body of the capsule. Each arm of the wing desirably lies within an angular space more than 75° and preferably not more than 90° from the axis of the body. A preferred way of providing the preferential bending is to form the wing with a generally wide flat cross section and with reinforcing ribs along its forward or convex side, for example, with one or more central ribs extending a short distance outward from the central point of attachment of the wing to the end of the capsule and with longer edge ribs extending a greater distance along the edges of such arms.

The capsule preferably comprises an elongated tubular body having a delivery end and containing a solid charge or pre-formed core of agent-containing administrative composition. The delivery end contains a peripheral wall defining a delivery opening, and the charge of composition contained in the body is biased, as by a piston and spring, toward and against such wall to maintain a supply of composition at the delivery opening over a prolonged period, and to maintain sealing engagement of the charge with the end wall as the charge is reduced by delivery of composition through the delivery opening to the rumen. The delivery end of the capsule is preferably formed with an end wall defining a circumferentially continuous and axially symmetrical frustoconical inner face about a central delivery opening, which inner face merges at its periphery with a smoothly curved border surface which progressively converges from the inner suface of the side wall to the frustoconical surface. The charge or core of administrative composition is adapted to be weakened adjacent its end surface by exposure through the delivery opening to ruminal fluid. The border surface serves to make initial sealing contact with the end edges of a pre-formed core of composition, and during use to maintain that peripheral seal and to guide the edge portions of the charge inward toward the delivery opening. The width of frustoconical surface engaged by the weakened end of the charge and the solubility or flow characteristics of the charge may be varied to control the rate of progression of the administrative charge toward the delivery opening and thereby to control the rate of delivery of the administrative composition from the capsule. The inner end of the charge may be protected from exposure to ruminal fluid, as by sealing the forward end of the capsule or by using a sealing piston.

The capsule is conveniently molded of two parts, preferably with one part including the barrel and the delivery opening and defining an inside surface of uniform cross section to receive a capsule with predetermined clearance and to slidably receive the piston, and with the other part formed as a cap or closure for the forward end of the capsule and carrying the wing as an integral part of the molding. The capsule must have adequate strength and resilience to permit its wings to be folded during insertion through the esophagus and to ensure their return to outstanding position. The wings should also have sufficient fatigue resistance to withstand repeated physical stresses in the rumen, and it is believed the present invention improves fatigue resistance. The material of the capsule must be acceptable in the rumen of the living animal, and must withstand the chemical and biologic conditions there present. The capsules may be made of any material having suitable characteristics, and we have found it desirable to mold them of copolymers of polyethylene and polypropylene, or preferably, of polypropylene itself.

Suitable compositions for the charge or pre-formed core to be used in the capsules will depend on the nature of the active agent or agents to be administered and on the rate and period of administration. Cores for administering a growth stimulant or anti-bloat agent to range animals over a prolonged period of, say, up to 200 days or more, desirably have a mode of operation in which the end surface of the core exposed to ruminal temperature and fluid will absorb water or other components from the ruminal fluid and in which this will change the characteristics of the solid composition in such a way that the core will swell or become weakened or both. When this occurs at the end area of the charge exposed through the delivery opening of the capsule, the desirable result occurs that the composition will be discharged to or washed or eroded into the ruminal fluid at a rate determined by controlling factors such as the nature of the composition and especially the configuration of the delivery end wall and the size of its opening. As the administrative composition is lost to the rumen, the charge or core of composition will be progressively and continuously moved by the piston and spring to compensate for such loss and to maintain the remaining portion of the charge or core with its end in sealed relation with the converging end wall about the delivery opening. Such sealed relation is important both initially when the core is first deposited in the rumen and continuously during its operation so as to prevent the ruminal fluid from acting on other portions of the charge and causing it to swell or weaken. The configuration of the end wall about the opening is found to accomplish this result.

Additional features and advantages of the invention will become apparent from the following description of embodiments of the invention.

The accompanying drawings illustrate the invention and show preferred embodiments exemplifying the best mode of carrying out the invention as presently perceived. In such drawings:

FIG. 1 is a substantially full-scale longitudinal section of a capsule in accordance with the invention, with the arms of the retention wing shown in full lines in their normal extended positions and shown in dotted lines in their folded administration positions for insertion of the capsule through an esophagus;

FIG. 2 is a section taken on the line 2—2 of FIG. 1;

FIG. 3 is a front elevational view of the wing and forward end of the capsule;

FIGS. 4, 5, and 6 are sectional views taken on the lines 4—4, 5—5, and 6—6 of FIG. 3;

FIG. 7 is a longitudinal section like FIG. 1, but on an enlarged scale and with a mid-portion of the barrel omitted and with the parts at the forward end of the capsule in partially exploded relation;

FIG. 8 is a diagrammatic view of an administration tool for inserting a capsule by mouth into the esophagus of a bovine animal;

FIG. 9 is a fragmental sectional view showing a capsule barrel containing a modified form of piston adapted to seal against the inside face of the barrel;

FIG. 10 is a side elevation of a smaller capsule adapted for use in sheep; and

FIG. 11 is a front end elevation of the capsule shown in FIG. 10.

The capsule shown in FIGS. 1–7 of the drawings comprises a body 10 having a closure cap 12 at its forward end which carries a retention wing 14. The body 10 has a generally cylindrical barrel 16 joined in a smooth curve to an end wall 18 defining a constricted circular discharge opening 20. The end wall has a circumferentially continuous frustoconical inner face 17 at an included angle of about 120° surrounding the central opening 20, which face merges at its periphery to a border surface 19 which progressively converges in a smooth curve from the inner surface of the side wall of the capsule to such frustoconical surface 17.

The forward end of the barrel 16 has a conical mouth 22 leading to an inward-open groove 24 adapted to receive and interlock with corresponding parts on the forward cap 12. Such cap 12 has a generally hemispherical wall 26 joined at the rear to a flange 28 having an external bead 30 adapted to enter through the mouth 22 of the barrel and engage in locked relation with the groove 24 to mechanically secure the cap 12 to the body. The barrel 16 contains an administrative charge in the form of a pre-formed cylindrical core 32 which, as formed and as shown in FIG. 1, has a rounded end face 34 adapted to make initial sealing engagement with the inner face 19 of the barrel. In FIG. 7, the rear or delivery end of the core 32 is shown in a condition it takes during use, in which the core end has been weakened by absorption or ruminal fluid and pressed toward the delivery opening 20 and against the end wall 18. The core 32 is engaged at its other end by a piston 36 which is biased in a direction to urge the core 32 against that constriction wall 18. As shown, the biasing means is a light coil spring 38 having its rearward end received in the cup-shaped piston 36. Desirably, the hemispherical end wall of the cap 12 is formed internally with a pair of cross ribs 40 which form a flat seat for the opposite end of the spring 38.

The retention wing 14 is integrally connected and attached to the cap 12 adjacent the axis of the capsule body at the outermost central portion of the hemispherical wall 26 by a connection 42 over an area which lies on and close to the axis of the capsule. The wing 14 is substantially tangent to the hemispherical cap 12 on that central axis and has arms 44 extending outward in opposite directions from that point of attachment, as shown in FIGS. 1 and 4. The arms are adapted to be resiliently bent downward along the curved hemispherical outer surface of the cap 12 and to be brought substantially flat against the wall of the barrel, as shown in dotted lines in FIG. 1, so as to present a cross section of effective diameter not much larger than the barrel itself when the capsule is conditioned for insertion through the esophagus into the rumen of an animal. When the capsule passes from the esophagus into the large rumen, the arms 44 of the wing 14 spring outward to their fully extended positions so as to block passage of the capsule back through the esophagus and thus to retain the capsule against regurgitation or passage from the rumen.

The outstanding, substantially right-angular position of the wing arms 44 is considered advantageous both in preventing regurgitation of the capsule and to reduce bending and stress of the arms in the rumen, in that in a right-angular T-shape, the capsule is less likely than would be the case with other configurations to have its arms bent relative to each other or the barrel. More especially, such contractions and working are less likely to bend both arms to a position which would allow the forward end of the capsule to enter the esophagus.

The wing 14 is desirably reinforced and made so that its arms 44 bend more easily back toward and against the sides of the capsule than forward in the opposite direction, away from the capsule, as would be required for the capsule to pass rear end first back through the esophagus. In some cases, the wing as molded takes a slightly arched shape so that its arms 44 are arched rearward toward the capsule, and hence so that less bending is required to bring them against the side of the capsule than to swing them in the opposite direction to a corresponding position. Each arm 44 desirably has a normal position in which it lies at or beyond an angle of 75° and preferably not beyond an angle of 90° from the side or axis of the capsule.

The central portion of the wing is reinforced and desirably made of asymmetric cross section to increase the resistance of the wing to bending of its arms in a forward direction. As shown, an asymmetric configuration is obtained by forming longitudinal ribs on the outer surface of the wing. Thus, as shown in FIGS. 3-6, the basic cross section of the wing is that of a leaf spring in the form of a wide flat rectangle as shown in FIG. 4. Inward of FIG. 4, as shown in FIG. 5, the wing is formed with two upstanding side ribs 46 along its edges which, when the wing is bent against the capsule, extend over a substantial portion of its length along the barrel 16 of the capsule. Still further inward, the wing is formed with a shorter central rib 48 which extends across the area 42 of attachment of the wing to the wall 26 of the cap. The rib 48 is desirably of a length to extend substantially to the base of the hemispherical wall 26 when the arms are bent to insertion position, as shown in FIGS. 3 and 8. The ribs 46 and 48 reinforce the wing 14 against forward bending, and thus give the wing greater resistance to forward bending than to the rearward bending which is required to carry its arms against the sides of the capsule barrel 16.

In a particular embodiment, a capsule for use in cattle comprised a barrel approximately 6¼ inches (156 mm) long and 1¼ inches (31 mm) in outside diameter, and a wing ½ inch (12.5 mm) wide and 6½ inches (162.5 mm) long with side ribs 46 extending 60% of the length of the wing and a center rib 48 half the length of the side ribs, the wing being attached to the cap over a circular area having a diameter of about 0.375 inch (9.4 mm).

This configuration and construction of the wing and its interrelation with the curved capsule end formed by the hemispherical wall 26 not only facilitates insertion of the capsule through the esophagus and retention of the capsule in the rumen, but also enhances the ability of the capsule to withstand the conditions to which it is subjected in the rumen during its prolonged stay. In the rumen, the capsule and wing are subjected not only to chemical and biological conditions which it must withstand, but also to continuing and forceful mechanical stresses from the undigested food in the rumen and the movements of the contents of the rumen during the normal course of entrance, regurgitation, and digestion.

The capsule shown is readily assembled by inserting a pre-formed cylindrical core 32 into the barrel 16 of the body portion 10, inserting a piston 36 and spring 38 behind the capsule, and compressing the spring and pressing a cap 12 into the open end of the barrel 16 so that the rib 30 of the cap interlocks with the groove 24 of the barrel. Various other means may be used to secure the cap to the barrel and, if desired, to seal the joint between them, including, for example, sonic or other welding procedures.

Before such assembly, a lubricant such as a light silicone lubricant is desirably applied either to the inner surface of the barrel 16 or to the outer surface of the core 32. Such lubricant provides an initial seal, gives some waterproofing for the pre-formed core, and forms a barrier film to prevent adhesion of the core to the barrel. This will help to ensure that the core 32 will slide in the barrel and will be initially pressed by the light spring 38 into sealing engagement with the end wall 18 and maintained in engagement therewith throughout the long period of sustained release of the capsule composition at the delivery opening 20 of the capsule.

The body 10 and cap 12 of the capsule are both adapted to be readily and inexpensively molded from plastic material. Such material must, of course, be capable of resisting the chemical, biological, and physical conditions encountered in the rumen, and we have found that capsules molded of polypropylene best withstand such conditions. In some instances, capsules may need to remain in the rumen for extended period of time, since in some parts of the world cattle remain on the range for such periods, and capsules may be administered periodically over that period. Cattle to which capsules are administered may have weights of upward from 300 pounds, and in such cattle the rumen may have a volume on the order of twelve gallons or more, so that the presence of capsules of the size here contemplated can be tolerated in plural numbers and over long periods.

Insertion of a capsule into the rumen in cattle is conveniently done with an administration tool as shown in FIG. 8. Such tool comprises a tubular barrel 60 having an open end adapted to receive a capsule 10 with its wing arms 44 folded against the sides of its barrel 16. The barrel 60 is mounted on a tube 62 having a handle portion 64 by which the barrel can be manipulated through the mouth of the animal to place the end of the capsule 10 in the esophagus. The tube 64 contains a thrust rod or cable 66 having a plunger 68 at its forward end and a thrust knob 70 at its outer end by which the plunger head 68 can be advanced to discharge the capsule 10 from the barrel 60 into the esophagus. When the capsule with its folded arms 44 is thus discharged partway into the esophagus, the capsule will then move on through the esophagus into the rumen, and the esophagus will hold the arms 44 in folded position until the capsule reaches the rumen. The arms will then spring outward to their normal outstanding position shown in full lines in FIG. 1 so as to retain the capsule in the rumen.

When the arms 44 of the wing 16 are bent to folded position, as indicated in dotted lines in FIG. 1, such arms bend in an arc on a long radius, in the clearance provided by and following the curved outer surface of the hemispherical wall 12 of the capsule so as not to be stressed to a point of strain, and when the arms are released from their folded position in the rumen, they tend strongly to return to their outstanding positions in diametrically opposite directions from the axis of the capsule, preferably with a slight arch as shown in FIG. 1. In such position, the wing presents a substantially flat outer face which tends to prevent the forward end of the capsule from entering the esophagus to be regurgitated from the rumen. If the opposite end of the capsule should enter the rumen, the outspread wing and its high resistance to bending in the opposite direction will prevent the capsule from passing through the esophagus and will thus prevent its regurgitation in that position. Further, the outspread arms 44 of the wing are so widely spaced angularly from each other and from the capsule that the working of the rumen has little tendency to bend the arms toward the capsule, and they are not so readily squeezed toward the capsule as arms at an acute angle to each other and to the barrel.

When a pre-formed core 32 is first inserted in the barrel 16, the spring 38 presses its end edge into sealing engagement with the end wall 18 of the barrel so as to limit contact of the ruminal fluid to the end surface 34 of the core. In normal operation, such ruminal fluid migrates into the end of the core 32 and tends to soften and weaken it, and the core is then urged by the spring 38 toward the opening 20 in the end wall of the capsule. The capsule is thus held in sealed relation with the end wall 18 over a wide area as shown in FIG. 7, and the area of access to ruminal fluid to the end of the capsule 32 is limited by the size of the opening 20. Over that access area, the composition of the capsule 32 will be discharged to the ruminal fluid, as by washing, erosion, and dissolution. Meanwhile, the migration of ruminal fluid, or components thereof, into the end portion of the core will progress to maintain an equilibrium of softened material at the end of the core, which will be maintained by progressive movement of the core toward the discharge opening by the spring 38. This will produce a sustained administration of medicaments contained in the core to the rumen over a prolonged period. The rate of such administration will depend in part on the composition of the core 32, but wil also be controlled in an important respect by the configuration of the end wall 18 of the capsule, as here shown and described, and especially by the outward-converging conical portion 17 thereof. The size of the opening 20 and the width of the conical face 17 may be changed to vary the rate of administration.

It is desirable to protect the sides and rear end of the core 32 in the capsule from contact with ruminal fluid which might tend to cause it to swell excessively against the sides of the barrel and prevent forward movement of the core 32 toward the end wall 18 to maintain sealing contact at that point. Either of two methods may be used to accomplish this purpose. In the capsules of FIGS. 1-7, the piston 36 is formed with a flat end 35 and a cylindrical side wall 37 which fits loosely within the barrel 16 so that it will slide freely along the inside of the barrel as the material of the core 32 is consumed and so as to maintain the core in continuing sealing engagement with the end wall 18 of the barrel. With the use of such a loose-fitting and non-sealing piston 36, the displacement or spring chamber behind the piston will not be sealed by the piston, and hence is desirably sealed against entrance of ruminal fluid. Such sealing may be obtained by sealing the joint between the open end of the barrel 16 and the wall 26 of the cap 12, as by sonic sealing, by running a hot iron around a joint, or by applying a sealing material to the joint.

With a sealed capsule, there are indications that the active agent contained in the core or charge of composition may be delivered to the animal in an initial surge or pulse and that the rate of administration then decreases and remains substantially constant over a prolonged period. We are not sure why this initial pulse occurs, but believe it may be in part because of an initial increase in pressure in the spring chamber. Such increase could be caused by the change in temperature from an ambient temperature to a ruminal temperature of about 39° C. A pressure increase could also be caused by a higher rate of diffusion through the walls of the capsule of gases such as carbon dioxide from the rumen into the capsule than the rate of diffusion of nitrogen outward from the air contained in the spring chamber.

In the modification shown in FIG. 9, the capsule comprises a body barrel 116 which is formed with a reasonably true and accurate internal cylindrical surface. The core is pressed forward by a piston 136 having a flat front end 135 and a generally cylindrical side wall 137. Such side wall has a portion with a sliding fit in the barrel 116, and extends rearward in spaced relation with such side walls and is provided with a rear skirt 139 formed to make resilient sealing contact with the cylindrical inner surface of the barrel. With the piston thus sealed to the barrel, the joint between the barrel and the rear cap can be left unsealed, as by using a mechanically interfitting joint as shown in FIG. 7 which is not hermetically sealed. Such unsealed joint will permit entrance of sufficient ruminal fluid, especially gas, into or out of the spring chamber to avoid the occurrence of either an increase or a decrease in pressure which would tend to add to or offset the force of the spring 138 on the piston 136.

The modified capsule shown in FIGS. 10 and 11 is adapted for use in smaller animals, particularly in sheep. This is similar in construction to the capsule of FIG. 1, in that it comprises a barrel 216 having a rear end wall 218 formed with a discharge opening 220. The forward end of the barrel 216 is closed by a hemispherical cap 212 which is attached to the barrel by an interlocking joint as in FIG. 7. A wing 214 is attached to the center of the hemispherical cap 212 and comprises arms 244 extending in opposite directions substantially at right angles to the axis of the capsule. The capsule is adapted to contain a core 232 of a composition containing the desired active agent or agents and to contain a piston and spring, not shown, analogous to those of the modification of FIGS. 1-7.

In a particular embodiment of a capsule for use in sheep, the capsule at an overall length of 3.753 inches (95.35 mm) and a diameter of 0.708 inch (18 mm), and carried a wing having a length of approximately 4.2 inches (105 mm) with a cross section of 0.236 inch (6 mm) by 0.040 inch (1 mm). The end opening in the barrel had a diameter of 0.236 inch (6 mm). The wing was attached to the cap over a central circular area having a diameter slightly greater than the width of the wing.

The smaller sheep capsule shown in FIGS. 10 and 11 is administered to sheep in a manner analogous to the administration of the cattle capsule, and acts in an analogous manner. While the wing of the smaller sheep capsule is of uniform cross section throughout its length and not reinforced with ribs nor bowed as in the cattle capsule, the sheep capsule has been used successfully and has been found to be retained in the sheep rumen for prolonged periods.

What is claimed is:

1. A sustained release capsule adapted to be retained in the rumen of a ruminant animal for delivery of an administrative composition thereto over a prolonged period, comprising
   an elongated tubular body containing an administrative composition and including a delivery area for delivery of such composition to the rumen,
   retention arms attached to the body for retaining the capsule in the rumen, said arms being attached to the capsule body at junctions spaced inward from the sides of the body and having resiliently bendable portions extending from such junctures outward to such sides, and the body having curved surfaces along which such arm portions may bend, said arms normally standing outward from the body and being bendable along such curved surfaces so as to be moved from such normal outstanding positions to administration positions along the sides of the body for passage through the esophagus into the rumen of the animal and being adapted to resiliently return to their normal outstanding positions in the rumen.

2. A capsule as in claim 1 in which the capsule body has a convex curved end face extending substantially through a semicircular angle, the arms are attached to the body adjacent the center of such convex face and generally tangent thereto, the arms being bendable along such curved end face as they are moved from outstanding to administrative positions.

3. A capsule as in claim 2 in which the convex end face of the capsule body is generally hemispherical.

4. A capsule as in claim 3 in which the arms are substantially continuous so as to form a wing extending across the end of the capsule.

5. A capsule as in claim 4 in which the wing has at least one reinforcing rib on its forward face and extending continuously across the area of attachment of the wing to the capsule body.

6. A capsule as in claim 5 in which the wing has a plurality of reinforcing ribs on its forward face extending continuously across the juncture of the wing with the capsule body and extending different distances therefrom toward the ends of the arms.

7. A capsule as in claim 1 in which the arms are formed to have relatively less resistance to bending rearward from their outstanding positions toward their administration positions and relatively greater resistance to bending forward from their outstanding positions.

8. A capsule as in claim 7 in which the arms are of asymmetric cross section toward their inner ends so as to be more resistant to bending in one direction than the other.

9. A capsule as in claim 7 in which each arm has one or more longitudinal reinforcing ribs on its forward face so as to increase its resistance to forward bending.

10. A capsule as in claim 1 in which said tubular body contains a piston and means biasing such piston against the adminstrative composition for urging such composition toward said delivery area to maintain a supply of the composition at such area, and in which said piston is movable in sealed relation with the tubular body and the body forms a displacement chamber behind the piston which has limited communication with the outside so as to equalize pressure therebetween.

11. A sustained release capsule adapted to be retained in the rumen of a ruminant animal for delivery of an administrative composition thereto over a prolonged period, comprising
    an elongated tubular body containing an administrative composition and including an end delivery area for delivery of such composition to the rumen,
    means for retaining the capsule in the rumen,
    said tubular body defining a cylinder in which said administrative composition is movable toward said delivery area, a piston movable in said cylinder, and a spring biasing the piston against the composition to move it progressively to the delivery area to maintain a supply thereof at the delivery area, said piston having sealing engagement with the cylinder for preventing access of ruminal fluid from the chamber behind the piston to the composition, and vent means for equalizing pressure between such chamber and the outside of the capsule.

12. A sustained release capsule adapted to be introduced through the esophagus into the rumen of a ruminant animal for retention therein to deliver an administrative composition thereto over a prolonged period, comprising
    an elongated tubular barrel having a tubular side wall, an apertured constricting end wall at the rear end, and an open front end,
    a cap and means to secure the same in closing relation with the front end of the barrel to form a capsule body,
    said cap having a convex forward end and a plurality of retention arms attached to the cap and extending generally tangent to such end so as to have normal outstanding positions relative to the body,
    said retention arms being resiliently bendable over a long arc along said convex forward end of the cap to an administration position alongside said body for introduction through the esophagus, and being adapted to return to their outstanding normal positions when in the rumen.

13. A capsule as in claim 12 in which said barrel is cylindrical and said cap is generally hemispherical and said arms are attached to the cap over a restricted area substantially on the axis of the barrel.

* * * * *

Disclaimer 4,416,659.—*Barbara E. Simpson*, and *Norman A. Gervais*, Indianapolis, Ind. SUSTAINED RELEASE CAPSULE FOR RUMINANTS. Patent dated Nov. 22, 1983. Disclaimer filed Mar. 2, 1984, by the assignee, *Eli Lilly and Co.*

Hereby enters this disclaimer to all claims of said patent.
*[Official Gazette April 24, 1984.]*